(12) United States Patent
Missel et al.

(10) Patent No.: US 7,943,162 B2
(45) Date of Patent: *May 17, 2011

(54) DRUG DELIVERY DEVICE

(75) Inventors: Paul J. Missel, Arlington, TX (US); Yoseph Yaacobi, Fort Worth, TX (US)

(73) Assignee: Alcon, Inc., Hunenberg (CH)

( * ) Notice: Subject to any disclaimer, the term of this patent is extended or adjusted under 35 U.S.C. 154(b) by 1137 days.

This patent is subject to a terminal disclaimer.

(21) Appl. No.: 11/567,892

(22) Filed: Dec. 7, 2006

(65) Prior Publication Data

US 2007/0092570 A1 Apr. 26, 2007

Related U.S. Application Data

(63) Continuation-in-part of application No. 10/957,910, filed on Oct. 4, 2004, now abandoned, which is a continuation of application No. 10/186,960, filed on Jul. 1, 2002, now Pat. No. 6,808,719, which is a continuation of application No. 09/660,000, filed on Sep. 12, 2000, now Pat. No. 6,413,540.

(60) Provisional application No. 60/160,673, filed on Oct. 21, 1999.

(51) Int. Cl.
*A61F 2/00* (2006.01)
*A61F 13/00* (2006.01)
*A61K 9/00* (2006.01)

(52) U.S. Cl. ........ 424/427; 424/422; 424/423; 424/426; 424/428; 424/429

(58) Field of Classification Search .................. None
See application file for complete search history.

(56) References Cited

U.S. PATENT DOCUMENTS

| 3,416,530 | A | 12/1968 | Ness |
| 3,828,777 | A | 8/1974 | Ness |
| 4,014,335 | A | 3/1977 | Arnold |
| 4,256,108 | A | 3/1981 | Theeuwes |
| 4,300,557 | A | 11/1981 | Refojo et al. |
| 4,327,725 | A | 5/1982 | Cortese et al. |
| 4,624,848 | A | 11/1986 | Lee |
| 4,853,224 | A | 8/1989 | Wong |
| 4,946,450 | A | 8/1990 | Erwin |
| 4,997,652 | A | 3/1991 | Wong |
| 5,147,647 | A | 9/1992 | Darougar |
| 5,164,188 | A | 11/1992 | Wong |
| 5,178,635 | A | 1/1993 | Gwon et al. |

(Continued)

FOREIGN PATENT DOCUMENTS

DE 40 22 553 A1 1/1992

(Continued)

OTHER PUBLICATIONS

R. A. Pontes de Carvalho, et al.; "Delivery from Episcleral Exoplants"; Investigative Ophthamology & Visual Science; vol. 47, No. 10; Oct. 2006; pp. 4532-4539; 8 pgs.

(Continued)

*Primary Examiner* — Humera N Sheikh
(74) *Attorney, Agent, or Firm* — W. David Lee (57) ABSTRACT

Drug delivery devices, and methods of delivering pharmaceutically active agents to a target tissue within a body using such devices, are disclosed. One drug delivery device includes a body having an internal surface for disposing on a target tissue and a well having an opening to the internal surface. An inner core comprising a drug containing portion and an expandable material is disposed in the well.

3 Claims, 6 Drawing Sheets

U.S. PATENT DOCUMENTS

| | | | |
|---|---|---|---|
| 5,300,114 A | 4/1994 | Gwon et al. | |
| 5,322,691 A | 6/1994 | Darougar et al. | |
| 5,378,475 A | 1/1995 | Smith et al. | |
| 5,403,901 A | 4/1995 | Namdaran et al. | |
| 5,443,505 A | 8/1995 | Wong et al. | |
| 5,466,233 A | 11/1995 | Weiner et al. | |
| 5,466,466 A | 11/1995 | Müller | |
| 5,476,511 A | 12/1995 | Gwon et al. | |
| 5,516,522 A | 5/1996 | Peyman et al. | |
| 5,632,984 A | 5/1997 | Wong et al. | |
| 5,679,666 A | 10/1997 | Clark | |
| 5,710,165 A | 1/1998 | Kapin et al. | |
| 5,725,493 A | 3/1998 | Avery et al. | |
| 5,743,274 A | 4/1998 | Peyman | |
| 5,766,242 A | 6/1998 | Wong et al. | |
| 5,766,619 A | 6/1998 | Aiache et al. | |
| 5,770,592 A | 6/1998 | Clark | |
| 5,773,019 A | 6/1998 | Ashton et al. | |
| 5,797,898 A | 8/1998 | Santini, Jr. et al. | |
| 5,824,072 A | 10/1998 | Wong | |
| 5,824,073 A | 10/1998 | Peyman | |
| 5,830,173 A | 11/1998 | Avery et al. | |
| 5,836,935 A | 11/1998 | Ashton et al. | |
| 5,860,994 A | 1/1999 | Yaacobi | |
| 5,883,108 A | 3/1999 | DeSantis, Jr. | |
| 5,902,598 A | 5/1999 | Chen et al. | |
| 5,904,144 A | 5/1999 | Hammang et al. | |
| 5,916,584 A | 6/1999 | O'Donoghue et al. | |
| 6,001,088 A | 12/1999 | Roberts et al. | |
| 6,001,386 A | 12/1999 | Ashton et al. | |
| 6,074,661 A | 6/2000 | Olejnik et al. | |
| 6,110,485 A | 8/2000 | Olejnik et al. | |
| 6,120,460 A | 9/2000 | Abreu | |
| 6,126,687 A | 10/2000 | Peyman | |
| 6,146,366 A | 11/2000 | Schachar | |
| 6,217,895 B1 | 4/2001 | Guo et al. | |
| 6,375,972 B1 | 4/2002 | Guo et al. | |
| 6,378,526 B1 | 4/2002 | Bowman et al. | |
| 6,397,849 B1 | 6/2002 | Bowman et al. | |
| 6,413,245 B1 | 7/2002 | Yaacobi | |
| 6,413,540 B1 | 7/2002 | Yaacobi | |
| 6,416,777 B1 | 7/2002 | Yaacobi | |
| 6,582,422 B2 | 6/2003 | Hess | |
| 6,669,950 B2 | 12/2003 | Yaacobi | |
| 6,713,081 B2 | 3/2004 | Robinson et al. | |
| 6,719,750 B2 | 4/2004 | Varner et al. | |
| 6,808,719 B2 | 10/2004 | Yaacobi | |
| 7,195,774 B2 | 3/2007 | Carvalho et al. | |
| 7,276,050 B2 | 10/2007 | Franklin | |
| 2002/0188282 A1 | 12/2002 | Greenberg | |
| 2003/0175324 A1 | 9/2003 | Robinson et al. | |
| 2004/0071761 A1 | 4/2004 | Miller et al. | |
| 2004/0180075 A1 | 9/2004 | Robinson et al. | |
| 2004/0219181 A1 | 11/2004 | Viscasillas | |
| 2007/0112318 A1 | 5/2007 | Leahy et al. | |

FOREIGN PATENT DOCUMENTS

| | | |
|---|---|---|
| EP | 0 904 787 A1 | 3/1999 |
| RU | 2149615 C1 | 5/2000 |
| WO | WO 94/05257 | 3/1994 |
| WO | WO 95/26734 | 10/1995 |
| WO | WO 95/28984 | 11/1995 |
| WO | WO 96/36377 | 11/1996 |
| WO | WO 97/14415 | 4/1997 |
| WO | WO 98/23228 | 6/1998 |
| WO | WO 98/43611 | 10/1998 |
| WO | WO 99/07418 | 2/1999 |
| WO | WO 99/11244 | 3/1999 |
| WO | WO 99/32104 | 7/1999 |
| WO | WO 99/45920 | 9/1999 |
| WO | WO 00/37066 | 6/2000 |
| WO | WO 00/56340 | 9/2000 |
| WO | WO 01/49226 A1 | 7/2001 |
| WO | WO 02/053128 A2 | 7/2002 |
| WO | WO 02/058667 A2 | 8/2002 |
| WO | WO 02/100318 A2 | 12/2002 |
| WO | WO 03/020172 A1 | 3/2003 |
| WO | WO 2004/073551 A2 | 9/2004 |

OTHER PUBLICATIONS

"Bausch & Lomb and Control Delivery Systems Agree to Develop Breakthrough Therapeutic Products for Severe Eye Diseases," Business Wire via First!; NewsEdge Corp.; Jun. 14, 1999; 4 pp.

"Method of Placing Irrigation System into Tenon's Space," E.I. Sidorenko, et al.; Abstract of Russian Patent No. RU 2123314, issued Dec. 20, 1998; 1 pg.

"A New Method for Posterior Sub-Tenon's Drug Administration," Nesterov, et al.; Ophthalmic Surgery, vol. 24, No. 1, Jan. 1993; pp. 59-61.

Dialog(R) File 266:FEDRIP database record; Identifying, No. 122098; "Implantation of a Sub-Tenon Drug Delivery Device Loaded with a Test Article in Rabbits and Distribution of the Test Article in Ocular Tissues;" Compiled and distributed by NTIS; 1 pg; Jun. 3, 1999.

Dialog(R) File 266:FEDRIP database record; Identifying No. 134284; "Implantation of a Sub-Tenon Drug Delivery Device Loaded with a Test Article in Rabbits and Distribution of the Test Article in Ocular Tissues;" Compiled and distributed by NTIS; 1 pg., (2000).

Dialog(R) File 266:FEDRIP database record; Identifying No. 131476; "Ocular Bioavailability of AL-3789 and AL-4940 After Sub-Tenon's Injection of AL-3789 Ophthalmic Suspensions in New Zealand White Rabbits;" Compiled and distributed by NTIS; 1 pg., (2000).

DRUG DELIVERY DEVICE

This application is a continuation-in-part of U.S. application Ser. No. 10/957,910 filed Oct. 4, 2004 now abandoned, which is continuation of U.S. application Ser. No. 10/186,960 filed Jul. 1, 2002, now U.S. Pat. No. 6,808,719, which is a continuation of U.S. application Ser. No. 09/660,000, filed Sep. 12, 2000, now U.S. Pat. No. 6,413,540, which claims priority from U.S. Provisional Application No. 60/160,673, filed Oct. 21, 1999.

FIELD OF THE INVENTION

The present invention generally pertains to biocompatible implants for localized delivery of pharmaceutically active agents to body tissue. More particularly, but not by way of limitation, the present invention pertains to biocompatible implants for localized delivery of pharmaceutically active agents to the posterior segment of the eye.

DESCRIPTION OF THE RELATED ART

Several diseases and conditions of the posterior segment of the eye threaten vision. Age related macular degeneration (ARMD), choroidal neovascularization (CNV), retinopathies (i.e. diabetic retinopathy, vitreoretinopathy), retinitis (i.e. cytomegalovirus (CMV) retinitis), uveitis, macular edema, and glaucoma are several examples.

Age related macular degeneration (ARMD) is the leading cause of blindness in the elderly. ARMD attacks the center of vision and blurs it, making reading, driving, and other detailed tasks difficult or impossible. About 200,000 new cases of ARMD occur each year in the United States alone. Current estimates reveal that approximately forty percent of the population over age 75, and approximately twenty percent of the population over age 60, suffer from some degree of macular degeneration. "Wet" ARMD is the type of ARMD that most often causes blindness. In wet ARMD, newly formed choroidal blood vessels (choroidal neovascularization (CNV)) leak fluid and cause progressive damage to the retina.

In the particular case of CNV in ARMD, two main methods of treatment are currently being developed, (a) photocoagulation and (b) the use of angiogenesis inhibitors. However, photocoagulation can be harmful to the retina and is impractical when the CNV is near the fovea. Furthermore, photocoagulation often results in recurrent CNV over time. Oral or parenteral (non-ocular) administration of anti-angiogenic compounds is also being tested as a systemic treatment for ARMD. However, due to drug-specific metabolic restrictions, systemic administration usually provides sub-therapeutic drug levels to the eye. Therefore, to achieve effective intraocular drug concentrations, either an unacceptably high dose or repetitive conventional doses are required. Periocular injections of these compounds often result in the drug being quickly washed out and depleted from the eye, via periocular vasculature and soft tissue, into the general circulation. Repetitive intraocular injections may result in severe, often blinding, complications such as retinal detachment and endophthalmitis.

In order to prevent complications related to the above-described treatments and to provide better ocular treatment, researchers have suggested various implants aimed at localized delivery of anti-angiogenic compounds to the eye. U.S. Pat. No. 5,824,072 to Wong discloses a non-biodegradable polymeric implant with a pharmaceutically active agent disposed therein. The pharmaceutically active agent diffuses through the polymer body of the implant into the target tissue. The pharmaceutically active agent may include drugs for the treatment of macular degeneration and diabetic retinopathy. The implant is placed substantially within the tear fluid upon the outer surface of the eye over an avascular region, and may be anchored in the conjunctiva or sclera; episclerally or intrasclerally over an avascular region; substantially within the suprachoroidial space over an avascular region such as the pars plana or a surgically induced avascular region; or in direct communication with the vitreous.

U.S. Pat. No. 5,476,511 to Gwon et al. discloses a polymer implant for placement under the conjunctiva of the eye. The implant may be used to deliver neovascular inhibitors for the treatment of ARMD and drugs for the treatment of retinopathies, retinitis, and CMV retinitis. The pharmaceutically active agent diffuses through the polymer body of the implant.

U.S. Pat. No. 5,773,019 to Ashton et al. discloses a non-bioerodable polymer implant for delivery of certain drugs including angiostatic steroids and drugs such as cyclosporine for the treatment of uveitis. Once again, the pharmaceutically active agent diffuses through the polymer body of the implant.

All of the above-described implants require careful design and manufacture to permit controlled diffusion of the pharmaceutically active agent through a polymer body (matrix devices) or polymer membrane (reservoir devices) to the desired site of therapy. Drug release from these devices depends on the porosity and diffusion characteristics of the matrix or membrane, respectively. These parameters must be tailored for each drug moiety to be used with these devices. Consequently, these requirements generally increase the complexity and cost of such implants.

U.S. Pat. No. 5,824,073 to Peyman discloses an indentor for positioning in the eye. The indentor has a raised portion that is used to indent or apply pressure to the sclera over the macular area of the eye. This patent discloses that such pressure decreases choroidal congestion and blood flow through the subretinal neovascular membrane, which, in turn, decreases bleeding and subretinal fluid accumulation.

Therefore, a need exists in the biocompatible implant field for a surgically implantable drug delivery device capable of safe, effective, rate-controlled, localized delivery of a wide variety of pharmaceutically active agents to any body tissue. The surgical procedure for implanting such a device should be safe, simple, quick, and capable of being performed in an outpatient setting. Ideally, such a device should be easy and economical to manufacture. Furthermore, because of its versatility and capability to deliver a wide variety of pharmaceutically active agents, such an implant should be capable of use in clinical studies to deliver various agents that create a specific physical condition in a patient or animal subject. In the particular field of ophthalmic drug delivery, such an implantable drug delivery device is especially needed for localized delivery of pharmaceutically active agents to the posterior segment of the eye to combat ARMD, CNV, retinopathies, retinitis, uveitis, macular edema, and glaucoma.

SUMMARY OF THE INVENTION

In one aspect, the present invention is a drug delivery device including a body having an internal surface for disposing on a target tissue and a well having an opening to the internal surface. The device includes an inner core disposed in the well. The inner core includes a drug containing portion having a pharmaceutically active agent and a second surface proximate the opening. The inner core also includes an expandable material for maintaining the second surface proximate the opening when the expandable material is in contact with fluid from the target tissue.

BRIEF DESCRIPTION OF THE DRAWINGS

For a more complete understanding of the present invention, and for further objects and advantages thereof, reference is made to the following description taken in conjunction with the accompanying drawings in which.

DETAILED DESCRIPTION OF THE PREFERRED EMBODIMENTS

The preferred embodiments of the present invention and their advantages are best understood by referring to FIGS. 1 through 9 of the drawings, like numerals being used for like and corresponding parts of the various drawings.

Figure 1:
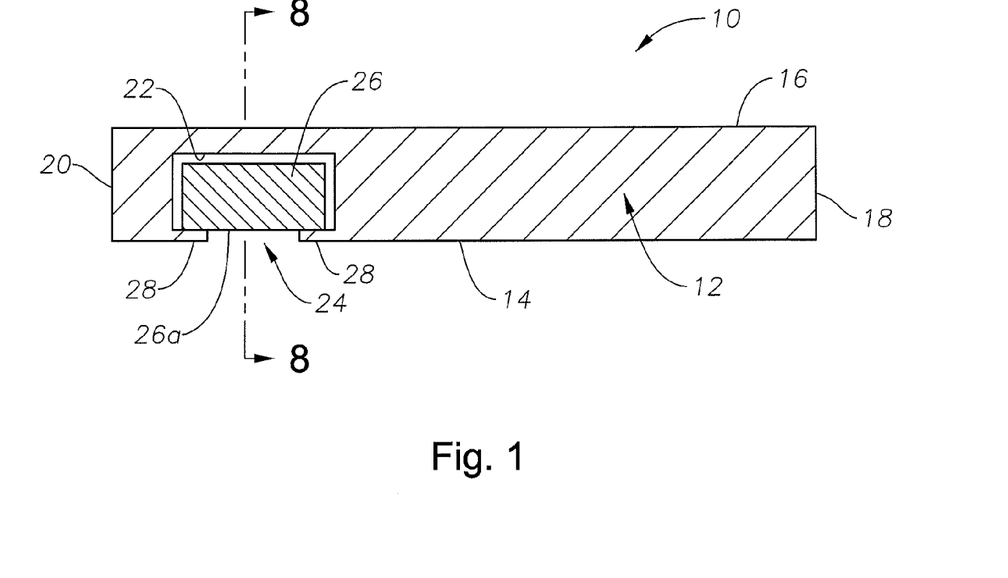
FIG. 1 is a side sectional view of a drug delivery device according to a preferred embodiment of the present invention.

FIG. 1 schematically illustrates a drug delivery device 10 according to a preferred embodiment of the present invention. Device 10 may be used in any case where localized delivery of a pharmaceutically active agent to body tissue is required. By way of example, device 10 may be used to treat a medical disorder of the eye, ear, nose, throat, skin, subcutaneous tissue, or bone. Device 10 may be used in humans or animals.

Device 10 generally includes a body 12 having an internal surface 14 and an external surface 16. As shown in FIG. 1, body 12 preferably has a generally rectangular three-dimensional geometry with a proximal end 18 and a distal end 20. Body 12 may have any other geometry that has an internal surface 14 for placement proximate a target tissue in the body of a patient. By way of example, body 12 may have a cylindrical, an oval, a square, or other polygonal three-dimensional geometry.

Body 12 includes a well or cavity 22 having an opening 24 to internal surface 14. An inner core 26 is preferably disposed in well 22. Inner core 26 is preferably a tablet comprising one or more pharmaceutically active agents. Alternatively, inner core 26 may comprise a conventional hydrogel having one or more pharmaceutically active agents disposed therein. A retaining member 28 is preferably disposed proximate opening 24. Retaining member 28 prevents inner core 26 from falling out of well 22. When inner core 26 is a cylindrical tablet, retaining member 28 is preferably a continuous rim or lip disposed circumferentially around opening 24 having a diameter slightly less than the diameter of tablet 26. Alternatively, retaining member 26 may comprise one or more members that extend from body 12 into opening 24. Although not shown in FIG. 1, inner core 26 may alternatively comprise a suspension, solution, powder, or combination thereof containing one or more pharmaceutically active agents. In this embodiment, internal surface 14 is formed without opening 24, and the suspension, solution, powder, or combination thereof diffuses through the relatively thin portion of internal surface 14 below inner core 26. Still further in the alternative, device 10 may be formed without well 22 or inner core 26, and the pharmaceutically active agent(s) in the form of a suspension, solution, powder, or combination thereof may be dispersed throughout body 12 of device 10. In this embodiment, the pharmaceutically active agent diffuses through body 12 into the target tissue.

The geometry of device 10 maximizes communication between the pharmaceutically active agent of inner core 26 and the tissue underlying internal surface 14. Internal surface 14 preferably physically contacts the target tissue. By way of example, if the target tissue has a generally flat surface, device 10 would be appropriate for the delivery of a pharmaceutically active agent. As another example, if the target tissue has a generally convex surface, a device 10a shown in FIG. 2 having a generally concave internal surface 14a designed to mate with such a target surface may be utilized. Corners 30 of proximal end 18a, and corners 32 of distal end 20a, may be slanted and/or rounded off to facilitate surgical placement of device 10a and to maximize comfort to the patient. Retaining member 28 is preferably designed with a minimum thickness necessary to retain inner core 26 so as to dispose a surface 26a of inner core 26 in close proximity to the target tissue. Although not shown in FIGS. 1 or 2, inner core 26 may be formed so that surface 26a physically contacts the target tissue.

Figure 2:
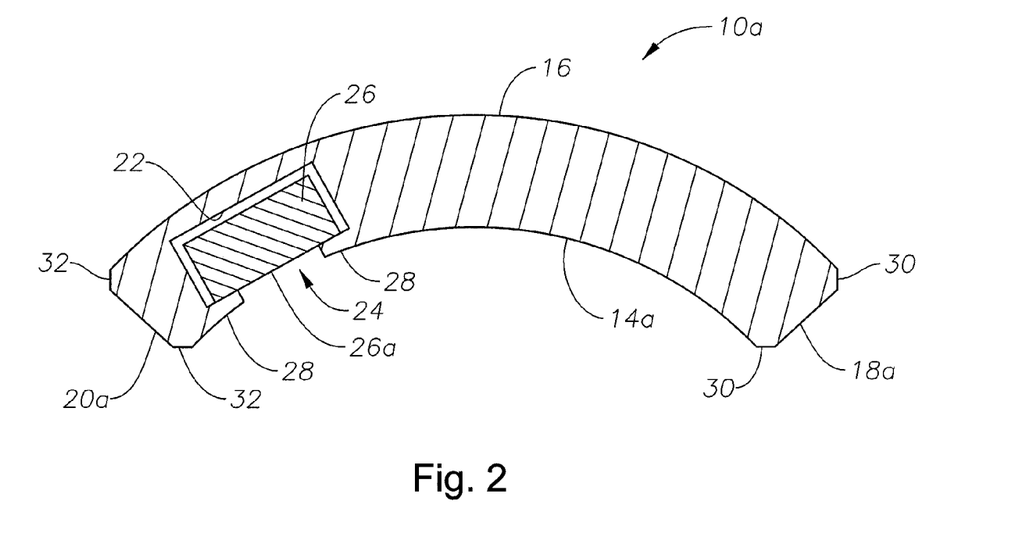
FIG. 2 is a side sectional view of a second drug delivery device according to a preferred embodiment of the present invention.

Alternatively, device 10 or 10a may be disposed in the body of a patient so that internal surface 14 or 14a is disposed proximate the target tissue. In this case, internal surface 14 or 14a physically contacts intermediate tissue disposed between it and the target tissue. The pharmaceutically active agent of inner core 26 communicates with the target tissue through opening 24 and this intermediate tissue.

Referring again to FIG. 1, body 12 preferably comprises a biocompatible, non-bioerodable material. Body 12 more preferably comprises a biocompatible, non-bioerodable polymeric composition. Said polymeric composition may be a homopolymer, a copolymer, straight, branched, cross-linked, or a blend. Examples of polymers suitable for use in said polymeric composition include silicone, polyvinyl alcohol, ethylene vinyl acetate, polylactic acid, nylon, polypropylene, polycarbonate, cellulose, cellulose acetate, polyglycolic acid, polylactic-glycolic acid, cellulose esters, polyethersulfone, acrylics, their derivatives, and combinations thereof. Examples of suitable soft acrylics are more fully disclosed in U.S. Pat. No. 5,403,901, which is incorporated herein in its entirety by reference. Said polymeric composition most preferably comprises silicone. Of course, said polymeric composition may also comprise other conventional materials that affect its physical properties, including, but not limited to, porosity, tortuosity, permeability, rigidity, hardness, and smoothness. Exemplary materials affecting certain ones of these physical properties include conventional plasticizers, fillers, and lubricants. Said polymeric composition may comprise other conventional materials that affect its chemical properties, including, but not limited to, toxicity, hydrophobicity, and body 12 - inner core 26 interaction. Body 12 is preferably impermeable to the pharmaceutically active agent of inner core 26. When body 12 is made from a generally elastic polymeric composition, the diameter of well 22 may be slightly less than the diameter of inner core 26. This frictional fit secures inner core 26 within well 22. In this embodiment, body 12 may be formed without retaining member 28, if desired.

Inner core 26 may comprise any pharmaceutically active agents suitable for localized delivery to a target tissue. Examples of pharmaceutically active agents suitable for inner core 26 are anti-infectives, including, without limitation, antibiotics, antivirals, and antifungals; antiallergenic agents and mast cell stabilizers; steroidal and non-steroidal anti-inflammatory agents; combinations of anti-infective and anti-inflammatory agents; decongestants; anti-glaucoma agents, including, without limitation, adrenergics, β-adrenergic blocking agents, a-adrenergic agonists, parasypathomimetic agents, cholinesterase inhibitors, carbonic anhydrase inhibitors, and prostaglandins; combinations of anti-glaucoma agents; antioxidants; nutritional supplements; drugs for the treatment of cystoid macular edema including, without limitation, non-steroidal anti-inflammatory agents; drugs for the treatment of ARMD, including, without limitation, angiogenesis inhibitors and nutritional supplements; drugs for the treatment of herpetic infections and CMV ocular infections; drugs for the treatment of proliferative vitreoretinopathy including, without limitation, antimetabolites and fibrinolytics; wound modulating agents, including, without limitation, growth factors; antimetabolites; neuroprotective drugs, including, without limitation, eliprodil; and angiostatic steroids for the treatment of diseases or conditions of the posterior segment of the eye, including, without limitation, ARMD, CNV, retinopathies, retinitis, uveitis, macular edema, and glaucoma. Such angiostatic steroids are more fully disclosed in U.S. Pat. Nos. 5,679,666 and 5,770,592, which are incorporated herein in their entirety by reference. Preferred ones of such angiostatic steroids include 4,9(11)-Pregnadien-17α,21-diol-3,20-dione and ,9(11)-Pregnadien-17α,21-diol-3,20-dione-21-acetate. Inner core 26 may also comprise conventional non-active excipients to enhance the stability, solubility, penetrability, or other properties of the active agent or the drug core.

If inner core 26 is a tablet, it may further comprise conventional excipients necessary for tableting, such as fillers and lubricants. Such tablets may be produced using conventional tableting methods. The pharmaceutically active agent is preferably distributed evenly throughout the tablet. In addition to conventional tablets, inner core 26 may comprise a special tablet that bioerodes at a controlled rate, releasing the pharmaceutically active agent. By way of example, such bioerosion may occur through hydrolosis or enzymatic cleavage. If inner core 26 is a hydrogel, the hydrogel may bioerode at a controlled rate, releasing the pharmaceutically active agent. Alternatively, the hydrogel may be non-bioerodable but allow diffusion of the pharmaceutically active agent.

Device 10 may be made by conventional polymer processing methods, including, but not limited to, injection molding, extrusion molding, transfer molding, and compression molding. Preferably, device 10 is formed using conventional injection molding techniques. Inner core 26 is preferably disposed in well 22 after the formation of body 12 of device 10. Retaining member 28 is preferably resilient enough to allow inner core 26 to be inserted through opening 24 and then to return to its position as shown in FIG. 1.

Device 10 is preferably surgically placed proximate a target tissue. The surgeon first makes an incision proximate the target tissue. Next, the surgeon performs a blunt dissection to a level at or near the target tissue. Once the target tissue is located, the surgeon uses forceps to hold device 10 with internal surface 14 facing the target tissue and distal end 20 away from the surgeon. The surgeon then introduces device 10 into the dissection tunnel, and positions device 10 with internal surface 14 facing the target tissue. Once in place, the surgeon may or may not use sutures to fix device 10 to the underlying tissue, depending on the specific tissue. After placement, the surgeon sutures the opening and places a strip of antibiotic ointment on the surgical wound.

The physical shape of body 12, including the geometry of internal surface 14, well 22, opening 24, and retaining member 28, facilitate the unidirectional delivery of a pharmaceutically effective amount of the pharmaceutically active agent from inner core 26 to the target tissue. In particular, the absence of a polymer layer or membrane between inner core 26 and the underlying tissue greatly enhances and simplifies the delivery of an active agent to the target tissue.

Device 10 can be used to deliver a pharmaceutically effective amount of a pharmaceutically active agent to target tissue for many years, depending on the particular physicochemical properties of the pharmaceutically active agent employed. Important physicochemical properties include hydrophobicity, solubility, dissolution rate, diffusion coefficient, and tissue affinity. After inner core 26 no longer contains active agent, a surgeon may easily remove device 10. In addition, the "preformed" tunnel facilitates the replacement of an old device 10 with a new device 10.

FIGS. 3 through 6B schematically illustrate an ophthalmic drug delivery device 50 according to a preferred embodiment of the present invention. Device 50 may be used in any case where localized delivery of a pharmaceutically active agent to the eye is required. Device 50 is particularly useful for localized delivery of active agents to the posterior segment of the eye. A preferred use for device 50 is the delivery of pharmaceutically active agents to the retina proximate the macula for treating ARMD, choroidial neovascularization (CNV), retinopathies, retinitis, uveitis, macular edema, and glaucoma. Of course, device 50 may also be utilized for localized delivery of pharmaceutically active agents to body tissue other than the eye, if desired.

Figure 3:
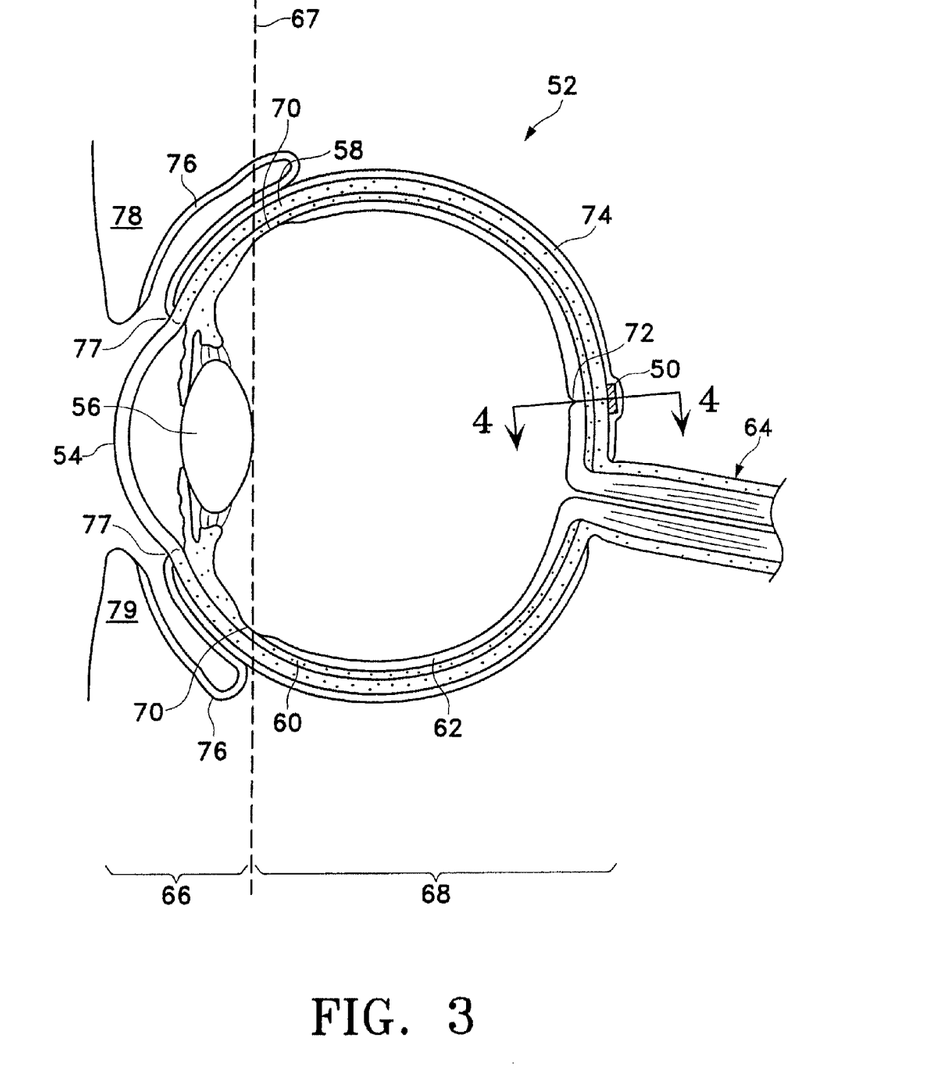
FIG. 3 is a side sectional view schematically illustrating the human eye.
Figure 4:
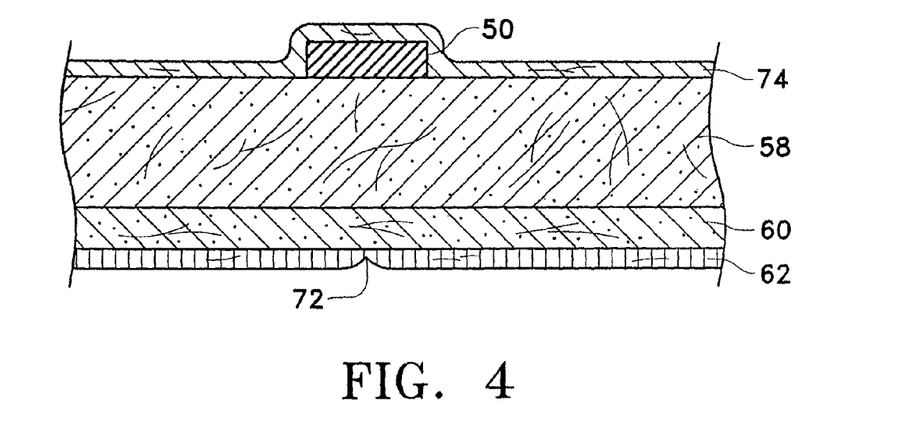
FIG. 4 is detailed cross-sectional view of the eye of FIG. 3 along line 4-4.

Referring first to FIG. 3, a human eye 52 is schematically illustrated. Eye 52 has a cornea 54, a lens 56, a sclera 58, a choroid 60, a retina 62, and an optic nerve 64. An anterior segment 66 of eye 52 generally includes the portions of eye 52 anterior of a line 67. A posterior segment 68 of eye 52 generally includes the portions of eye 52 posterior of line 67. Retina 62 is physically attached to choroid 60 in a circumferential manner proximate pars plana 70. Retina 62 has a macula 72 located slightly lateral to its optic disk. As is well known in the ophthalmic art, macula 72 is comprised primarily of retinal cones and is the region of maximum visual acuity in retina 62. A Tenon's capsule or Tenon's membrane 74 is disposed on sclera 58. A conjunctiva 76 covers a short area of the globe of eye 52 posterior to limbus 77 (the bulbar conjunctiva) and folds up (the upper cul-de-sac) or down (the lower cul-de-sac) to cover the inner areas of upper eyelid 78 and lower eyelid 79, respectively. Conjunctiva 76 is disposed on top of Tenon's capsule 74. As is shown in FIGS. 3 and 4, and as is described in greater detail hereinbelow, device 50 is preferably disposed directly on the outer surface of sclera 58, below Tenon's capsule 74 for treatment of most posterior segment diseases or conditions. In addition, for treatment of ARMD in humans, device 50 is preferably disposed directly on the outer surface of sclera 58, below Tenon's capsule 74, with an inner core of device 50 proximate macula 72.

Figure 5:
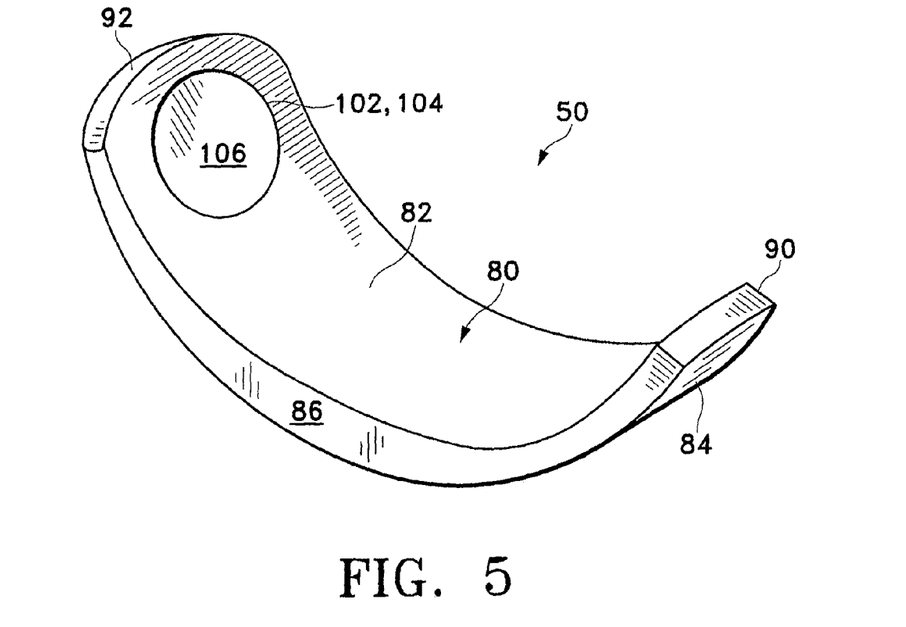
FIG. 5 is a perspective view of an ophthalmic drug delivery device according to a preferred embodiment of the present invention.
Figure 6A:
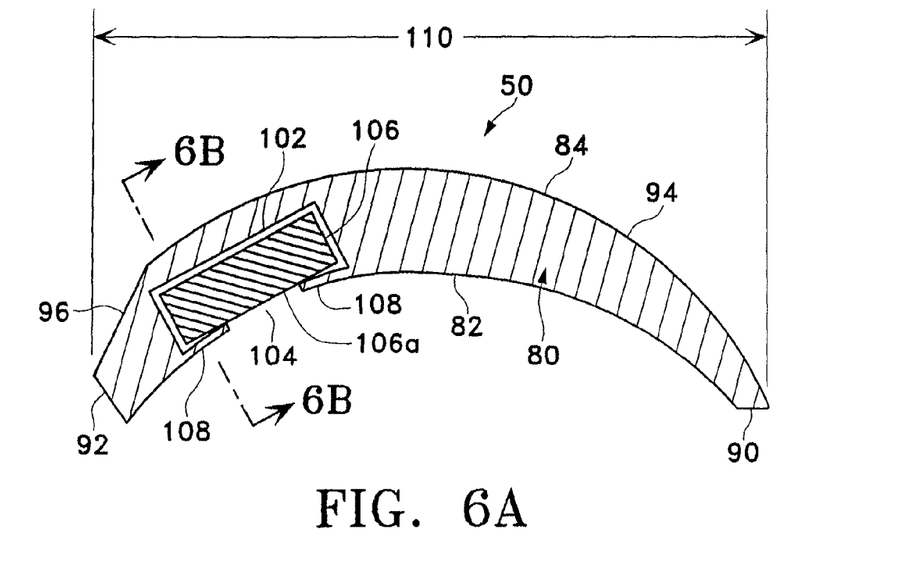
FIG. 6A is a side sectional view of the ophthalmic drug delivery device of FIG. 5.
Figure 6B:
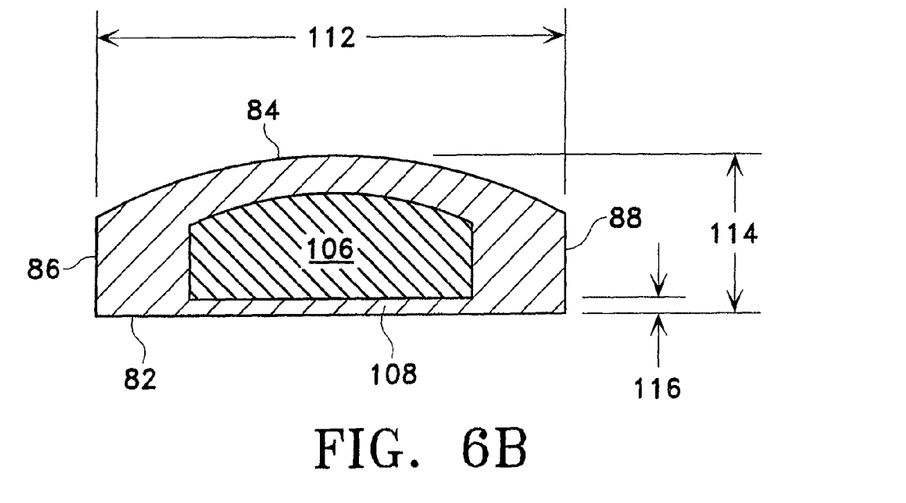
FIG. 6B is an enlarged cross-sectional view of the ophthalmic drug delivery device of FIG. 6A taken along line 6B-6B.

FIGS. 5, 6A, and 6B schematically illustrate drug delivery device 50 in greater detail. Device 50 generally includes a body 80 having a scleral surface 82 and an orbital surface 84. Scleral surface 82 is preferably designed with a radius of curvature that facilitates direct contact with sclera 58. Orbital surface 84 is preferably designed with a radius of curvature that facilitates implantation under Tenon's capsule 74. Body 80 preferably has a curved, generally rectangular three-dimensional geometry with rounded sides 86 and 88, proximal end 90, and distal end 92. As shown best in the side sectional view of FIG. 6A, orbital surface 84 preferably has tapered surfaces 94 and 96 proximate proximal end 90 and distal end 92, respectively, that facilitate sub-Tenon implantation of device 50 and enhance the comfort of the patient. Body 80 may alternatively have a geometry similar to that of device 10a shown in FIG. 2. In addition, body 80 may have any other geometry that has a curved scleral surface 82 for contact with sclera 58. By way of example, body 80 may have a generally cylindrical, oval, square, or other polygonal three-dimensional geometry.

Body 80 includes a well or cavity 102 having an opening 104 to scleral surface 82. An inner core 106 is preferably disposed in well 102. Inner core 106 is preferably a tablet comprising one or more pharmaceutically active agents. Alternatively, inner core 106 may comprise a conventional hydrogel having one or more pharmaceutically active agents disposed therein. A retaining member 108 is preferably disposed proximate opening 104. Retaining member 108 prevents inner core 106 from falling out of well 102. When inner core 106 is a cylindrical tablet, retaining member 108 is preferably a continuous rim or lip disposed circumferentially around opening 104 having a diameter slightly less than the diameter of tablet 106. Alternatively, retaining member 108 may comprise one or more members that extend from body 80 into opening 104. Although not shown in FIG. 6A, inner core 106 may alternatively comprise a suspension, solution, powder, or combination thereof containing one or more pharmaceutically active agents. In this embodiment, scleral surface 82 is formed without opening 104, and the suspension, solution, powder, or combination thereof diffuses through the relatively thin portion of scleral surface 82 below inner core 26. Still further in the alternative, device 50 may be formed without well 102 or inner core 106, and the pharmaceutically active agent(s) in the form of a suspension, solution, powder, or combination thereof may be dispersed throughout body 80 of device 50. In this embodiment, the pharmaceutically active agent diffuses through body 80 into the target tissue.

The geometry and dimensions of device 50 maximize communication between the pharmaceutically active agent of inner core 106 and the tissue underlying scleral surface 82. Scleral surface 82 preferably physically contacts the outer surface of sclera 58. Although not shown in FIGS. 6A or 6B, inner core 106 may be formed so that surface 106a physically contacts the outer surface of sclera 58. Alternatively, scleral surface 82 may be disposed proximate the outer surface of sclera 58. By way of example, device 50 may be disposed in the periocular tissues just above the outer surface of sclera 58 or intra-lamellarly within sclera 58.

Body 80 preferably comprises a biocompatible, non-bioerodable material. Body 80 more preferably comprises a biocompatible, non-bioerodable polymeric composition. The polymeric composition comprising body 80, and the polymers suitable for use in the polymeric compositions of body 80, may be any of the compositions and polymers described hereinabove for body 12 of device 10. Body 80 most preferably is made from a polymeric composition comprising silicone. Body 80 is preferably impermeable to the pharmaceutically active agent of inner core 106. When body 80 is made from a generally elastic polymeric composition, the diameter of well 102 may be slightly less than the diameter of inner core 106. This frictional fit secures inner core 106 within well 102. In this embodiment, body 80 may be formed without retaining member 108, if desired.

Inner core 106 may comprise any ophthalmically acceptable pharmaceutically active agents suitable for localized delivery. Exemplary pharmaceutically active agents include the pharmaceutically active agents listed hereinabove for inner core 26 of device 10. Inner core 106 may also comprise conventional non-active excipients to enhance the stability, solubility, penetrability, or other properties of the active agent.

If inner core 106 is a tablet, it may further comprise conventional excipients necessary for tableting, such as fillers and lubricants. Such tablets may be produced using conventional tableting methods. The pharmaceutically active agent is preferably distributed evenly throughout the tablet. In addition to conventional tablets, inner core 106 may comprise a special tablet that bioerodes at a controlled rate, releasing the pharmaceutically active agent. By way of example, such bioerosion may occur through hydrolosis or enzymatic cleavage. If inner core 106 is a hydrogel, the hydrogel may bioerode at a controlled rate, releasing the pharmaceutically active agent. Alternatively, the hydrogel may be non-bioerodable but allow diffusion of the pharmaceutically active agent.

Device 50 may be made by conventional polymer processing methods, including, but not limited to, injection molding, extrusion molding, transfer molding, and compression molding. Preferably, device 50 is formed using conventional injection molding techniques as described hereinabove for device 10.

Device 50 is preferably surgically placed directly on the outer surface of sclera 58 below Tenon's capsule 74 using a simple surgical technique that is capable of being performed in an outpatient setting. The surgeon first performs a peritomy in one of the quadrants of eye 52. Preferably, the surgeon performs the peritomy in the infra-temporal quadrant, about 3 mm posterior to limbus 77 of eye 52. Once this incision is made, the surgeon performs a blunt dissection to separate Tenon's capsule 74 from sclera 58, forming an antero-posterior tunnel. Once the tunnel is formed, the surgeon uses forceps to hold device 50 with scleral surface 82 facing sclera 58 and distal end 92 away from the surgeon. The surgeon then introduces device 50 into the tunnel in a generally circular motion to position inner core 106 of device 50 generally above the desired portion of retina 62. The surgeon then closes the peritomy by suturing Tenon's capsule 74 and conjunctiva 76 to sclera 58. After closing, the surgeon places a strip of antibiotic ointment on the surgical wound. Alternatively, the surgeon may suture proximal end 90 of device 50 to sclera 58 to hold device 50 in the desired location before closure of the tunnel.

In the case of ARMD in the human eye, the surgeon utilizes the above-described technique to position inner core 106 of device 50 in one of two preferred locations in the infra-temporal quadrant of eye 52. One preferred location is directly on the outer surface of sclera 58, below Tenon's capsule 74, with inner core 106 positioned proximate to, but not directly above, macula 72. A surgeon may position inner core 106 of device 50 at this location by moving distal end 92 of device 50 below the inferior oblique muscle in a direction generally parallel to the lateral rectus muscle. A second preferred location is directly on the outer surface of sclera 58, below Tenon's capsule 74, with inner core 106 positioned directly above macula 72. A surgeon may position inner core 106 of device 50 at this location by moving distal end 92 of device 50 toward macula 72 along a path generally between the lateral and inferior rectus muscles and below the inferior oblique muscle. For ARMD, the pharmaceutically active agent of inner core 106 is preferably one of the angiostatic steroids disclosed in U.S. Pat. Nos. 5,679,666 and 5,770,592.

The physical shape of body 80 of device 50, including the geometry of scleral surface 82, well 102, opening 104, and retaining member 108, facilitate the unidirectional delivery of a pharmaceutically effective amount of the pharmaceutically active agent from inner core 106 through sclera 58, choroid 60, and into retina 62. In particular, the absence of a polymer layer or membrane between inner core 106 and sclera 58 greatly enhances and simplifies the delivery of an active agent to retina 62.

It is believed that device 50 can be used to deliver a pharmaceutically effective amount of a pharmaceutically active agent to retina 62 for many years, depending on the particular physicochemical properties of the pharmaceutically active agent employed. Important physicochemical properties include hydrophobicity, solubility, dissolution rate, diffusion coefficient, and tissue affinity. After inner core 106 no longer contains active agent, a surgeon may easily remove device 50. In addition, the "pre-formed" tunnel facilitates the replacement of an old device 50 with a new device 50.

The following example illustrates effective drug delivery to a rabbit retina using a preferred embodiment and surgical technique of the present invention, but are in no way limiting.

EXAMPLE

A device 50 was surgically implanted on the outer surface of the sclera, below the Tenon's capsule, generally along the inferior border of the lateral rectus muscle of the right eye of twenty (20) New Zealand White rabbits using a procedure similar to that described hereinabove for implantation of device 50 on sclera 58 of eye 52. Device 50 was constructed as shown in FIGS. 5 through 6B, with the following dimensions. Body 80 had a length 110 of about 15 mm, a width 112 of about 7.0 mm, and a maximum thickness 114 of about 1.8 mm. Retaining member 108 had a thickness 116 of about 0.15 mm. Scleral surface 82 had a radius of curvature of about 8.5 mm and an arc length of about 18 mm. Inner core 106 was a cylindrical tablet with a diameter of about 5.0 mm and a thickness of about 1.5 mm. Opening 104 had a diameter of about 3.8 mm. Well 102 had a diameter of about 4.4 mm. The pharmaceutically active agent used in tablet 106 was 4,9(11)-Pregnadien-17α,21-diol-3,20-dione, an angiostatic steroid sold by Steraloids, Inc. of Wilton, N.H., and which is more fully disclosed in U.S. Pat. Nos. 5,770,592 and 5,679,666. The formulation of tablet 106 consisted of 99.75 weight percent 4,9(11)-Pregnadien-17α,21-diol-3,20-dione, and 0.25 weight percent magnesium stearate.

At one week after implantation, 4 rabbits were euthanized and their right eyes were enucleated. The device 50 was removed from the eyes, and the location of tablet 106 was marked on their sclerae. Following the removal of the anterior segment and the vitreous of each eye and inversion of the thus formed eye-cup, a 10 mm diameter circular zone of retinal tissue, concentric with and below the location of tablet 106 on the sclera, was harvested (the "target site"). A 10 mm diameter circular zone of retinal tissue was also harvested from a second site located remote from the target site and on the other side of the optic nerve. In addition, a 10 mm diameter circular zone of retinal tissue was harvested from a third site located between the second site and the target site. Similar 10 mm diameter circular zones of choroidal tissue were also harvested at the target site, second site, and third site. All these tissues were separately homogenized, and the concentration of angiostatic steroid in each of these tissues was determined via an ocular pharmacokinetic study using high performance liquid chromatography and mass spectrometry analysis (LC-MS/MS). This procedure was repeated at 3, 6, 9, and 12 weeks after implantation.

Figure 7:
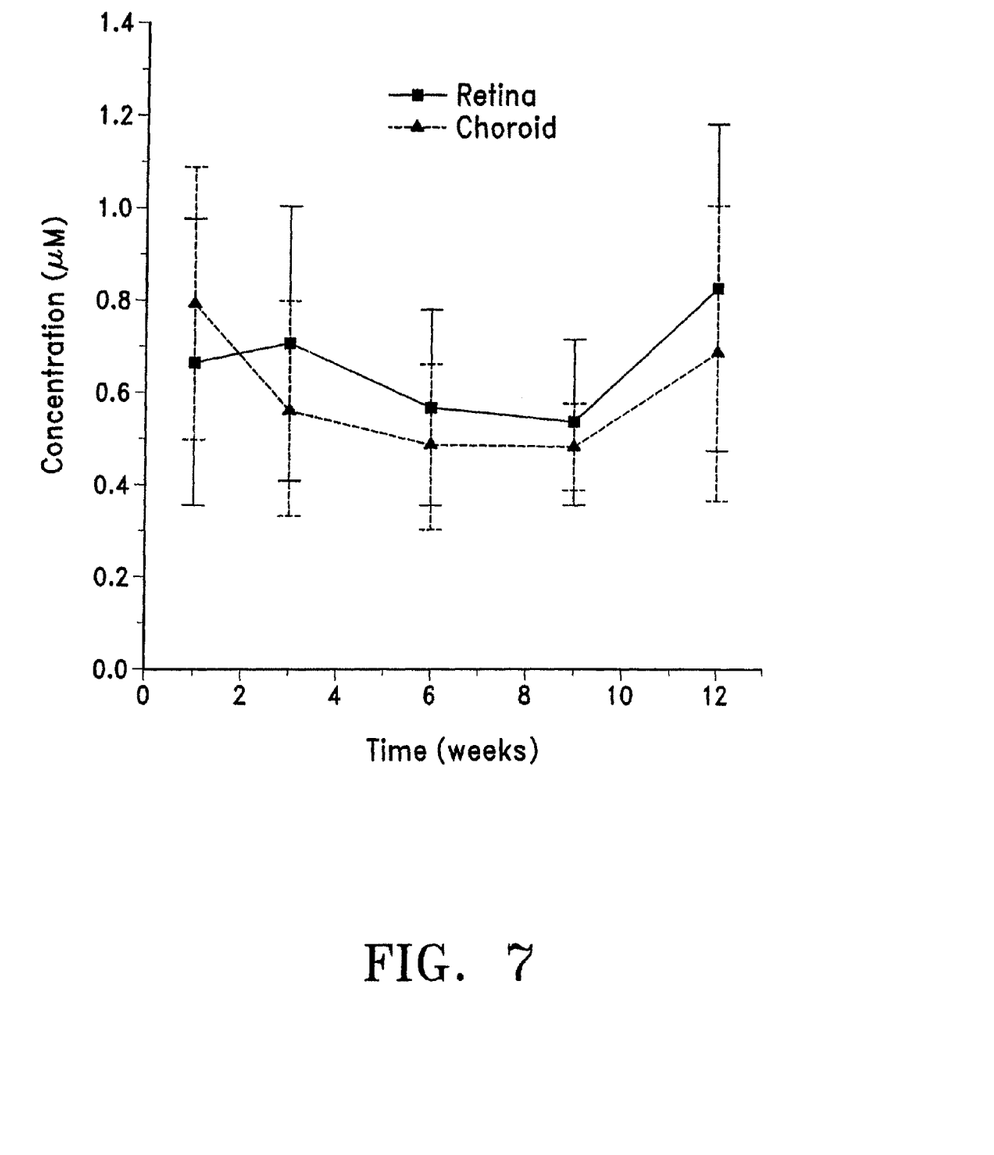
FIG. 7 is a graphical illustration of the results of a pharmacokinetic study with New Zealand White rabbits implanted with the ophthalmic drug delivery device of FIGS. 5 through 6B showing the mean concentration of a pharmaceutically active agent at a target site in the retina and choroid of the rabbits as a function of time.

FIG. 7 shows the mean concentration of 4,9(11)-Pregnadien-17α,21-diol-3,20-dione in the retina and the choroid at the target site as a function of time. The "error bars" surrounding each data point represent standard deviation. As shown in FIG. 7, device 50 delivered a pharmaceutically effective and generally constant amount of 4,9(11)-Pregnadien-17α,21-diol-3,20-dione to the retina and the choroid at the target site for a time period of up to twelve weeks. In contrast, the levels of 4,9(11)-Pregnadien-17α,21-diol-3,20-dione in the retina and the choroid at the second and third sites were at or near zero. Therefore, device 50 also delivered a localized dose of angiostatic steroid to the retina and the choroid at the target site.

Figure 8:
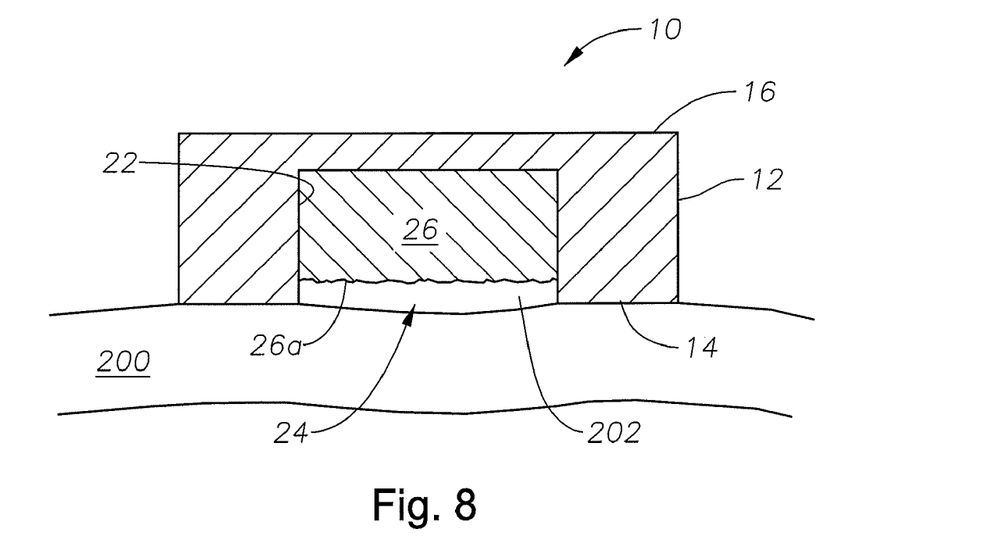
FIG. 8 is an enlarged cross-sectional view of the drug delivery device of FIG. 1 taken along line 8-8 shown after a period of use within target tissue.

FIG. 8 shows the drug delivery device 10 of FIG. 1 after a period of use in connection with a target tissue 200. In certain applications, such as when inner core 26 comprises a tablet comprising a pharmaceutically active agent, inner core 26 may erode after a period of use and create a gap 202 between target tissue 200 and surface 26a of inner core 26. In some instances, gap 202 may present a barrier to effective delivery of the pharmaceutically active agent from inner core 26 to target tissue 200. In other instances, gap 202 may allow tissue migration into well 22 that presents such a barrier.

Figure 9:
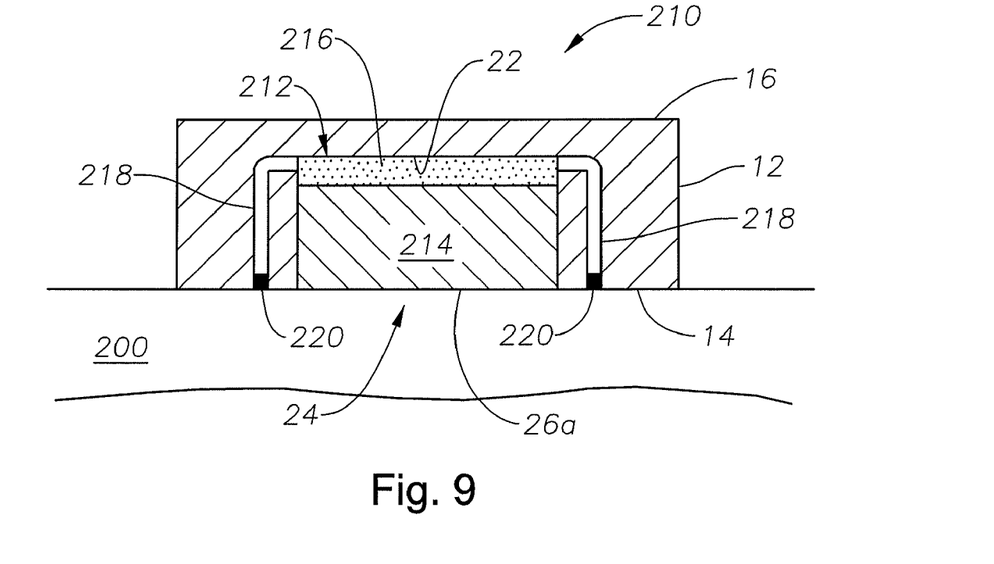
FIG. 9 is an enlarged cross-sectional view of a third drug delivery device according to a preferred embodiment of the present invention.

FIG. 9 schematically illustrates a drug delivery device 210 according to a preferred embodiment of the present invention. Drug delivery device 210 is substantially similar in construction and operation to drug delivery device 10, with the exception of inner core 212, one or more channels 218, and one or more plugs 220. Although drug delivery device 210 is described herein in connection with drug delivery device 10, inner core 212, channels 218, and plugs 220 are also applicable to drug delivery devices 10a and 50 described hereinabove as well as other drug delivery devices.

Inner core 212 preferably includes a drug containing portion 214 and an expandable material 216. Drug containing portion 214 may comprise any of the forms of inner core 26 of drug delivery device 10 or inner core 106 of drug delivery device 50. Drug containing portion 214 is preferably a tablet comprising a pharmaceutically active agent. Expandable material 216 may be any material that expands upon contact with a fluid. Expandable material 216 is preferably a hydrogel. Channels 218 are formed within body 12 of device 210 and are fluidly coupled to internal surface 14 and expandable material 216. Plugs 220 are formed within channels 218 proximate internal surface 14. Plugs 220 may be any porous material that allows the passage of water or other fluids but not tissue or other solids.

During use, fluid from the body contacts expandable material 216. Such fluid reaches expandable material 216 via channels 218. Alternatively, in certain applications, such fluid may reach expandable material 216 via passage through opening 24 and the space between the external surface of inner core 212 and well 22. In such applications, device 210 may be formed without channels 218 and plugs 220. Once in contact with fluid, expandable material 216 expands as needed within well 22 to insure that gap 202 is minimized or eliminated. Surface 26a thus remains in contact with, or in close proximity to, target tissue 200, and facilitates effective delivery of the pharmaceutically active agent from drug containing portion 214 to target tissue 200.

From the above, it may be appreciated that the present invention provides improved devices and methods for safe, effective, rate-controlled, localized delivery of a variety of pharmaceutically active agents to any body tissue. The surgical procedure for implanting such devices is safe, simple, quick, and capable of being performed in an outpatient setting. Such devices are easy and economical to manufacture. Furthermore, because of their capability to deliver a wide variety of pharmaceutically active agents, such devices are useful in clinical studies to deliver various agents that create a specific physical condition in a patient or animal subject. In the particular field of ophthalmic drug delivery, such devices are especially useful for localized delivery of pharmaceutically active agents to the posterior segment of the eye to combat ARMD, CNV, retinopathies, retinitis, uveitis, macular edema, and glaucoma.

It is believed that the operation and construction of the present invention will be apparent from the foregoing description. While the apparatus and methods shown or described above have been characterized as being preferred, various changes and modifications may be made therein without departing from the spirit and scope of the invention as defined in the following claims.

What is claimed is:

1. A drug delivery device, comprising:
    a body having an internal surface for disposing on a target tissue and a well having an opening to said internal surface; and
    an inner core disposed in said well, comprising:
        a tablet comprising a pharmaceutically active agent and a second surface disposed proximate said opening, wherein said pharmaceutically active agent is delivered to said target tissue from said tablet through said opening without having to pass through a polymer; and
        a hydrogel disposed between said tablet and an inner wall of said well opposite said opening, wherein said hydrogel expands to maintain said second surface proximate said opening as said tablet erodes over time and when said hydrogel is in contact with a fluid from said target tissue.

2. The drug delivery device of claim 1 wherein said body further comprises a channel separate from said well for communicating said fluid from said internal surface to said hydrogel.

3. The drug delivery device of claim 2 wherein said channel has a plug that allows passage of said fluid but not said tissue.

* * * * *